United States Patent [19]

Oppolzer

[11] Patent Number: 4,491,664

[45] Date of Patent: Jan. 1, 1985

[54] PROCESS FOR THE PRODUCTION OF ERGOT ALKALOIDS

[75] Inventor: Wolfgang Oppolzer, Vandoeuvres, Switzerland

[73] Assignee: Sandoz Ltd., Basel, Switzerland

[21] Appl. No.: 357,526

[22] Filed: Mar. 12, 1982

[30] Foreign Application Priority Data

Mar. 13, 1981 [GB] United Kingdom ............... 8107959

[51] Int. Cl.$^3$ ................... C07D 457/00; C07D 209/14
[52] U.S. Cl. ......................................... 546/67; 546/68;
546/69; 548/495; 548/500; 548/505; 548/507;
548/510
[58] Field of Search ............................. 546/67, 68, 61

[56] References Cited

U.S. PATENT DOCUMENTS 4,245,095  1/1981  Horwell et al. ..................... 546/68

FOREIGN PATENT DOCUMENTS 2500834  9/1982  France ................................. 546/67
2094798  9/1982  United Kingdom ................. 546/67

OTHER PUBLICATIONS

McOmie, J. F. W.; *Protective Groups in Organic Chemistry,* Plenum Press, New York, NY (1973).

*Primary Examiner*—Donald G. Daus
*Assistant Examiner*—G. Hendricks
*Attorney, Agent, or Firm*—Gerald D. Sharkin; Robert S. Honor; Thomas O. McGovern

[57] ABSTRACT

A process for the production of an ergot alkaloid comprising intramolecularly cyclizing a 3-iminoethyl-4-trans-buta-1',3'-dienylindole to produce an 8-ergolene and as necessary converting the resultant ergolene into the desired ergot alkaloid.

21 Claims, No Drawings

PROCESS FOR THE PRODUCTION OF ERGOT ALKALOIDS

This invention relates to a process for the production of ergot alkaloids, in particular derivatives of lysergic acid. The invention relates to ergot alkaloids produced in accordance with the process of the invention, as well as to novel intermediates employed in the process of the invention.

Ergot alkaloids are well known compounds with a tetracyclic nucleus of formula

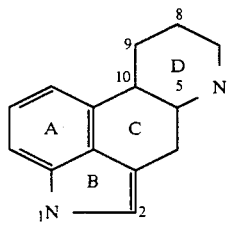

A double bond may be present in ring D in the ergolene sub-class e.g. in the 8,9 or in 9,10 position. The rings A, B, C and D may bear substituents e.g. as known in ergot chemistry, e.g., as described in "Ergot Alkaloids and related compounds" Ed. B. Berde and H. O. Schild, Springer-Verlag, 1978.

The ergolenes have two asymmetric centres giving rise to stereoisomerism in positions 5 and 10 (e.g. for 8-ergolenes) or 5 and 8 (for 9-ergolenes). Each of these ergolenes may therefore exist in racemic or optically active form.

One of the most important ergolenes is lysergic acid, which is a valuable intermediate for a wide variety of drugs useful in human therapy. The acid in optically active form may be obtained, for example, from ergot peptide alkaloids, occuring naturally or produced by fermentation, by alkaline hydrolysis.

Various total syntheses of lysergic acid and other ergot alkaloids have been described in the literature. These syntheses all suffer from various shortcomings, e.g. costly starting materials, low overall yields and many steps, e.g. because rings C and D are built up separately—with the result that none are completely satisfactory for commercial production.

The present invention provides a new synthesis of ergot alkaloids which is characterized by the simultaneous formation of rings C and D, the use of a few elegant steps to produce ergot alkaloids from known indole compounds, and satisfactory overall yields. Moreover, the synthesis may be employed for the preparation of a wide variety of ergot alkaloids bearing substituents, e.g. halogen atoms, or alkyl, alkoxy, hydroxy or optionally substituted amino groups. Substituents can be, for example, in the ring A and in the position 2.

Examples of such substituted compounds are 12-hydroxylysergic acid diethylamide, 13-bromo-dihydrolysergic acid, 2,13-dibromodihydrolysergic acid glycinamide, 2-chloro-6-methyl-8β-cyanomethylergoline, 1-methyl-dihydrolysergol, 1-formyl-dihydrohomolysergic acid nitrile, 12-hydroxy-dihydroergometrine 2-methyl-α-ergocryptine, 2-methyl-lysergic acid and 12-methoxymethergine, which are all known compounds.

An overview of the process of the present invention is presented in the following basic steps:

(i) producing a 3-iminoethyl-4-trans-buta-1',3'-dienylindole having the buta-1',3'-dienyl moiety in protected form and optionally having a protecting group on the iminoethyl moiety, (ii) deprotecting the trans buta-1',3'-dienyl moiety, (iii) intramolecularly cyclising the resultant 3-iminoethyl-4-trans-buta-1',3'-dienylindole to produce an 8-ergolene, which may then have the protecting group on the 6 position, and (iv) converting the resultant 8-ergolene as necessary into the desired ergot alkaloid.

The individual steps of the present process will be described in more detail below and illustrated with respect to a certain class of ergot alkaloids, it being appreciated that similar conditions may be employed for the production of other ergot alkaloids.

The steps may be visualized as follows:

(i) producing a compound of formula I

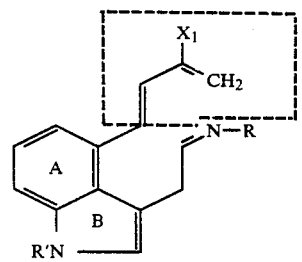

wherein the dotted line indicates that the trans-buta-1',3'-dienyl moiety is in protected form, $X_1$ is an inert group, R is a protecting group, and R' is a hydrogen or an imino-protecting group.

(ii) deprotecting the trans-buta-1',3'-dienyl-moiety in a compound of formula I to produce a compound of formula II

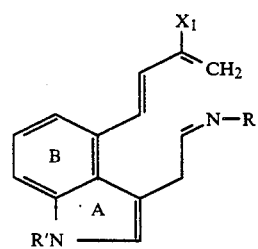

(iii) intramolecularly cyclising the resultant compound of formula II to produce a compound of formula III

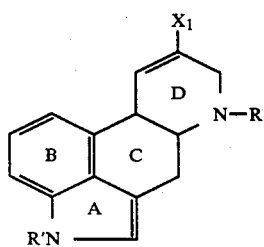

(iv) converting the resultant 8-ergolene as necessary into the desired ergot alkaloid.

The group $X_1$ may be chosen to be inert in basic steps (ii) and (iii). In basic step (iv) it may be converted, if desired, into a pharmacologically acceptable group or a group convertable into a pharmacologically acceptable group, e.g. COOH. Protecting group R or R' may be chosen such that they are inert in any one of basic steps (ii) to (iii). Such groups may then be converted into a pharmacologically acceptable group, or a group convertible into a pharmacologically acceptable group, in basic step (iv). Alternatively the protecting group may be chosen such that it is a pharmacologically acceptable group in which case it remains unchanged throughout the whole synthesis.

Suitable pharmacologically acceptable groups will be apparent to one skilled in the art.

The group $X_1$ may be any group known as a substituent in the 8 position of an ergot alkaloid, for example cyano, carbamoyl, carbamoyl mono-substituted e.g. by alkyl($C_{1-4}$), carbamoyl disubstituted e.g. by alkyl($C_{1-4}$) or an alkylidene($C_{3-5}$) chain, or hydroxymethyl($CH_2OH$), if desired with the hydroxy group in protected from. Preferably the group $X_1$ is alkoxy($C_{1-4}$)carbonyl, e.g. methoxycarbonyl.

R may be a group such that R—$NH_2$ is capable of forming an imino derivative with 3-indolylacetaldehyde, which is stable to high temperature, but which can be split off when desired under appropriate conditions.

R may be for example alkoxy($C_{1-4}$), acyloxy or optionally substituted benzyloxy.

Alternatively the imino derivative may be a hydrazone derivative, and R is e.g. amino, or amino substituted by ($C_{1-4}$)alkyl, acyl, or a sulphonyl group such as alkyl($C_{1-4}$)sulphonyl.

When R contains an acyl moiety, this is, for example, aliphatic acyl of 1 to 20, e.g. up to 5, carbon atoms. The acyl group may be optionally substituted, e.g. by one, two, or three substituents. Alternatively the acyl may be aromatic acyl, e.g. containing phenyl or phenylalkyl($C_{1-4}$) wherein the phenyl ring of either of the last two radicals may be optionally substituted. Where R contains substituted alkyl or phenyl moieties, suitable substituents include for example halogen, e.g. chlorine or fluorine, and ($C_{1-4}$)alkoxy.

R is preferably alkoxy.

R' may be an alkyl($C_{1-4}$). Alternatively R' may be e.g. a carbonyl group, e.g. an alkyl($C_{1-4}$)carbonyl group or a carboxylate group such as alkoxy($C_{1-4}$)carbonyl, or a sulphonyl group e.g. a tosyl group. It will be appreciated that the exact choice of protecting group will depend on the reaction conditions through which the group has to survive, and the reaction conditions used for splitting the group off. For the production of lysergic acid it is preferred to have $X_1$=COOAlk($C_{1-4}$); R=OCH$_3$ and R'=H.

In the last basic step (iv) of the process the starting material is an 8-ergolene.

The ergolene may contain a protecting group such as the group R as specified above in the 6 position. Moreover the ergolene maybe protected in the 1 position, e.g. by a group R' as specified above. Additionally the starting material may be a mixture of protected and unprotected forms when the basic step (iii) results in a mixture. Additionally the 8-ergolene may be mixed with the corresponding 9-ergolene when spontaneous isomerization has occurred during the basic step (iii).

Any protecting group may be split off, and converted into pharmacologically acceptable groups in conventional manner. The double bond may be hydrogenated, or isomerized, e.g. under basic conditions, to form a 9-ergolene and other interconversions, such as basic hydrolysis of any appropriate group $X_1$ to form a carboxylic acid group, effected to form ergot alkaloids useful as intermediates or pharmacologically active agents. Naturally these interconversions may be effected in any order.

The resultant compounds may be peptide or non-peptide ergot alkaloids, e.g. those described in "Ergot Alkaloids and Related Compounds" Ed. B. Berde and H. O. Schild, Springer Verlag, 1978.

If desired the ergot alkaloid in racemic form may be separated into individual optical isomer forms according to known procedures, e.g. fractional crystallization of diastereoisomeric salts. In the case of lysergic acid it is known to use the hydrazide derivative and fractionally crystallize the norephedride salt.

The ergot alkaloids having a protecting group, e.g. in the 6-position are particularly useful intermediates for the preparation of pharmacologically active ergot alkaloids. The provision of these ergot alkaloids is a particularly notable feature of the present invention.

In another aspect the present invention provides a process for the production of an ergot alkaloid which comprises deprotecting an ergot alkaloid bearing an imino protecting group in the 6-position to produce an ergot alkaloid unprotected in the 6-position and as necessary converting the resultant ergot alkaloid into the desired ergot alkaloid. The ergot alkaloid bearing a protecting group in the 6-position may have the formula IV:

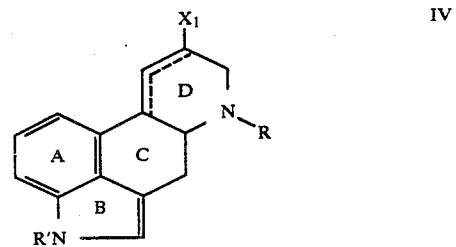

wherein $X_1$, R and R' are as defined above, and the dotted line signifies a double bond may be present in the 8,9 or 9,10 position.

Conveniently any protecting group in the 6-position is alkoxy.

In a further aspect the present invention provides a process for the production of an ergot alkaloid which comprises replacing an imino protecting group in the 6-position of a protected ergot alkaloid by a pharmacologically acceptable group.

The above-mentioned deprotecting and/or replacement steps may be effected in conventional manner. The exact reaction conditions will of course depend on the protecting group present. For example, when it is desired to produce alkylated derivatives, conventional alkylation agents may be used, if desired effecting the alkylation after splitting off the protecting group.

In a particularly elegant variation of the basic step (iv), an 8-ergolene is converted into a quaternary derivative of an ergot alkaloid which has attached to the nitrogen atom in the 6-position a pharmacologically acceptable group and a protecting group, which is then split off.

The present invention also provides a process comprising deprotecting a quaternary derivative of an ergot alkaloid which has attached to the nitrogen atom in the 6-position a pharmacologically acceptable group and a protecting group.

The ergot alkaloid quaternary derivative may have the formula V

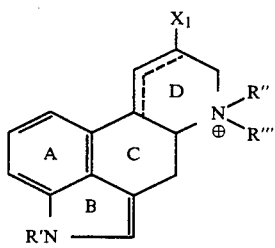

wherein $X_1$, R' are as defined above,

R" is a pharmacologically acceptable group, and

R''' is a protecting group.

Where the pharmacologically acceptable group (R") is alkyl and the protecting group (R''') is methoxy, it is convenient to use mild reducing conditions, e.g. amalgamated aluminium foil. Suitable temperatures are from about −5° C. to about 50° C. Preferably an aqueous solution, e.g. with an aprotic solvent, is employed.

The alkylation may be effected for example by using an alkyl fluorosulphate, or trimethyloxonium tetrafluoroborate salt. The reaction is conveniently effected at from about 0° C. to about 50° C. Preferably the reaction is effected in a organic solvent such as nitroethane or dichloromethane.

In the case of lysergic acid it is preferred to start from methyl 6-methoxy-8-ergolene-8-carboxylate, methylate this to form the 6-methyl quaternary salt, reduce the resultant compound with aluminium to give 6-methyl-8-ergolene-8-carboxylic acid, and treat the compound with alkali to produce lysergic acid.

It is to be appreciated that basic step (iv) need not be necessary in certain instances, when the product of basic step (iii) is the desired product, e.g. when $X_1$, R and R' are all pharmacologically acceptable groups.

Basic step (iii) concerns the simultaneous formation of rings C and D. This step is an important feature of the present invention. Accordingly in yet a further aspect the invention provides a process for the production of an ergot alkaloid which comprises intramolecularly cyclizing a 3-iminoethyl-4-trans-buta-1',3'-dienyl indole to produce an 8-ergolene, and as necessary converting the resultant ergolene into the desired ergot alkaloid.

The 3-iminoethyl-4-trans-buta-1',3'-dienyl indole may bear at least one protecting group and other substituents as necessary. The compound may have the formula II

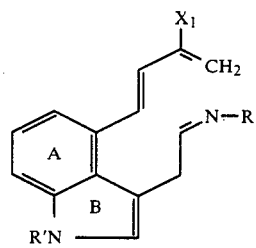

and the product will be of formula IV above wherein the double bond is in the 8,9 position, unless some isomerization to the 9,10 position has occurred.

The intramolecular cyclization may be effected in conventional manner for a Diels-Alder reaction using analogous starting materials. Naturally, the conditions should be chosen to minimize formation of dimers. It is preferred to keep the concentration of the compound of formula II as low as possible.

Preferably a high temperature is used, e.g. 150° C. to 800° C.

Preferably an inert gas atmosphere e.g. argon, is present.

The reaction may be effected in a solvent e.g. at about 180° to 250° C., preferably 200° C. Suitable solvents include phthalate esters, e.g. diethyl or dimethylphthalate, and substituted benzenes, e.g. 1,2,4-triisopropylbenzene, 1,2,4-trimethoxybenzene and particularly 1,2,4-trichlorobenzene.

Alternatively the reaction may be effected in the gas phase e.g. at 600° C. to 800° C.

As indicated above under these conditions some isomerization of the 8,9 double bond into the 9,10 position may occur.

The 3-iminoethyl-4-trans-buta-1',3'-dienyl indole may not be readily isolatable, so it is preferred to generate this compound in situ as a transient intermediate from a 3-iminoethyl-4-trans-buta-1',3'-dienyl indole having the trans-buta-1,3-dienyl moiety in protected form. This is accomplished in basic step (ii). In an elegant variation the butadienyl moiety is protected by a group which may be split off under the same reaction conditions used for basic step (iii). The deprotection accomplished in basic step (ii) is preferably effected under the same reaction conditions as basic step (iii).

For example the trans-buta-1,3-dienyl moiety may be protected in the form of a moiety

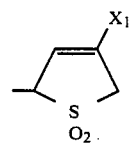 (a)

or in the form of a moiety (b)

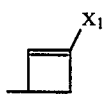 (b)

Preferably only the vinyl moiety of the trans-buta-1,3-dienyl moiety is protected and the compound of formula II obtained by removing the protecting group of compounds of formula VI

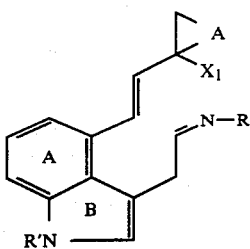

VI wherein $X_1$, R and R' are as defined above and A is a protecting group capable of being split off under the conditions of the intramolecular cyclization.

The protecting group A may be a moiety —S—. Alternatively it may be a moiety of formula (c)

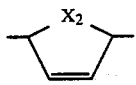

wherein $X_2$ is oxygen, sulphur or methylene optionally substituted by alkylidene with 1 to 4 carbon atoms, the ring being optionally substituted by one or two alkyl groups each containing 1 to 4 carbon atoms. It is to be appreciated that such compounds of formula VI may exist as endo and exo isomers and, if desired, be used as a mixture of such isomers.

In the case of when the protecting group A is moiety (c), the protecting group A, together with the two carbon atoms to which it is bound, suitably is of formula (d)

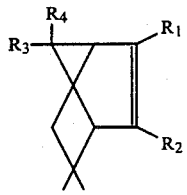

(d)

wherein $R_1$ and $R_2$ are both hydrogen or both methyl and $R_3$ and $R_4$ are both hydrogen or form together a group $=C(CH_3)_2$. Preferably, $R_1$, $R_2$, $R_3$ and $R_4$ are hydrogen.

A alternatively may be a moiety (e)

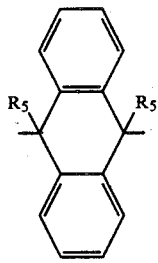

(e)

wherein $R_5$ is an inert group, e.g. hydrogen or alkyl($C_{1-4}$) (see H. Wohlweber, Diels Alder Reaktion, Thieme Verlag, 1962, p. 160).

If desired, the two step reaction, basic steps (ii) and (iii), may be carried out by very slow addition of a dilute solution of the compound of formula VI in an inert solvent, into the same solvent preheated to about 180°–250°, preferably 200°, under an inert gas atmosphere, e.g. argon.

The two-step reaction alternatively may be effected in the gas phase. For example, a compound of formula VI in an inert solvent may be slowly dropped into a vertically mounted quartz tube, filled with chips, e.g. of quartz, preheated to e.g. 600° to 800° C.

A gas stream may be used to sweep the vapours into a cooled zone where the product is collected.

The concentration of the compound of formula VI in the reaction mixture suitably does not exceed 5%. A 1% solution is preferred. Suitable solvents include the phthalate esters and substituted benzenes mentioned above.

Basic step (i) involves the production of 3-iminoethyl-4-trans-buta-1',3'-dienyl indole having the buta-1',3'-dienyl moiety in protected form. This may be accomplished in any of a wide variety of ways.

For example the starting material of formula VI may be prepared from a 4-hydroxymethyl indole according to the following scheme, e.g. as described in example 1, (a) to (g), hereinafter (Ts=tosyl):

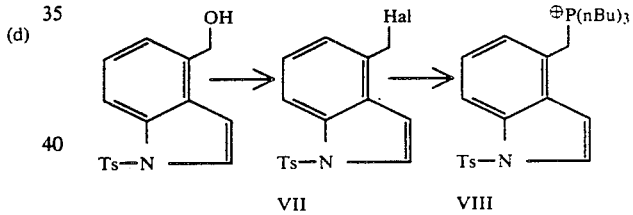

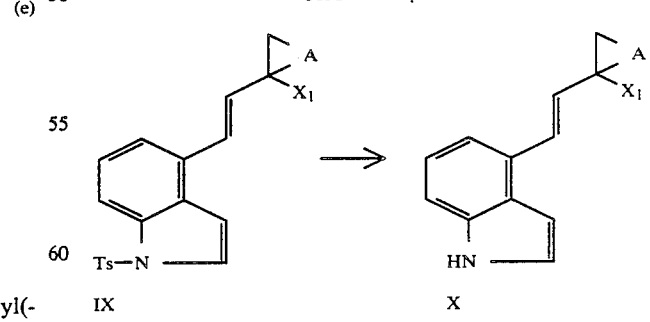

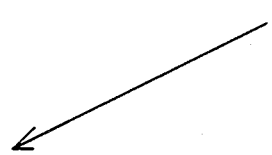

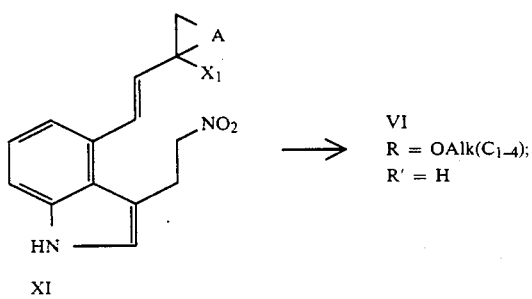

Following this scheme, the compounds of formula IX may be obtained by reacting the compound of formula VIII with a compound of formula XII

wherein A and $X_1$ as defined above.

The compounds of formula XII wherein A is a moiety c as defined above, wherein $X_2$ is $CH_2$ and $X_1$ is $COOCH_3$ may be obtained as a mixture of exo- and endo-isomers by formylation of the corresponding methyl bicyclo[2.2.1]hept-5-enyl-2-carboxylates. The formylation may be carried out by successive treatment with LDA and methylformate followed by chromatography ($SiO_2$). In this case, the product is believed to be the exo-formyl-ester of formula XII along with a side product arising from a $SiO_2$— promoted retro-Claisen rearrangement of the minor endo-formyl isomer which does not interfere with the subsequent Wittig reaction.

Wittig reaction of this mixture with the phosphorane derived from the compound of formula VIII may yield stereoselectively the (E)-vinylindoles of formula IX, e.g. in an aprotic polar solvent such as DMSO at a slightly elevated temperature such as 50°–100° C.

The nitroethylindols of formula XI may be obtained from the compounds of formula X by a Michael addition to nitroethylene. More efficiently, they may be obtained from the compounds of formula X in two steps, by a Mannich reaction followed by treatment of the crude Mannich product with nitromethane and dimethyl acetylenedicarboxylate according to the method of H. Plieninger and col., Liebigs Ann. Chem. 743, 95 (1971).

Transformation of the nitro compounds of formula XI to the oxime-ethers of formula VI may be achieved in one operation by reduction of the sodium nitronate derived from the compounds of formula XI with an excess of aq $TiCl_3/NH_4OAc$ in $MeOH/H_2O$ (3:1) in the presence of N-R-hydroxylamine (R being alkyl). The stable oxime ether of formula VI may be obtained as a mixture of syn- and anti-isomers and reacted further as such.

Insofar as the production of any particular starting material is not particularly described, this compound may be obtained in conventional manner, or in a manner analogous to that described herein.

In the following example, all temperatures are in degrees Centigrade and are uncorrected.

The heading compound of step (c) hereinafter may of course exist in two isomeric forms, namely the endo and exo forms. The product obtained according to e.g. NMR spectroscopy is isomerically pure. As the formation of the side product in step (c) may be rationalised easily on the basis of a Claisen rearrangement of the endo isomer it is believed that the heading compound has the exo configuration. This configuration will of course be maintained in the steps (d) to (g) hereinafter. Carbomethoxy=$COOCH_3$.

EXAMPLE (±)-Lysergic acid (a) 4-Bromomethyl-1-tosylindole (VII)

1.74 g (6.6 mmol) triphenylphosphine are added under nitrogen to a stirred solution of 1.0 g (3.33 mmol) 4-hydroxymethyl-1-tosylindole and 2.2 g (6.6 mmol) $CBr_4$ in 15 ml dry dimethylformamide. Stirring of the mixture at room temperature for 30 min, evaporation of the solvent at 0.05 Torr, filtration of the residue in $CH_2Cl_2$ through $SiO_2$ (50g) and trituration of the evaporated filtrate with n-hexane yields the crystalline bromide; m.p.: 113°–134.5°.

(b) 4-(Tributylphosphonio)methyl-1-tosylindole bromide (VIII)

A solution of 10.0 g (27.5 mmol) of the bromide obtained under (a) and 7.8 g (38.5 mmol) tri-n-butylphosphine in 150 ml dry benzene is heated at reflux under nitrogen for 2 hours. The resultant precipitate is filtered off, washed with ether and dried in vacuo to give the phosphonium salt; m.p.: 99°–105°.

(c) Methyl 2-formyl-bicyclo[2.2.1]hept-5-enyl-2-carboxylate (XII)

55 ml (0.11 mol of 2.0N n-butyllithium in hexane are added over 10 minutes to a stirred solution of 17 ml (0.12 mol) of diisopropylamine in 60 ml dry tetrahydrofuran under argon at −75°. The mixture is stirred at −75° for 30 minutes, 15.2 g (0.1 mol) methyl bicyclo[2.2.1]hept-5-enyl-2-carboxylate in 15 ml tetrahydrofuran at −75° is added and the mixture stirred at −75° for 1 hour. 15 ml (0.24 mol) methyl formate in 15 ml tetrahydrofuran is added slowly at −75°. The mixture is stirred at −75° for 2 hours and treated with 50 ml saturated aq. $NH_4Cl$ at −75°. Slow warming to room temperature, acidification to pH 5 with 1N HCl, extraction with ether, evaporation of the washed (sat. aq. $NH_4Cl$) and dried (on sodium sulphate) ether-phase and flash-chromatography (hexane/ethyl acetate 30:1→19:1) affords the formylester as an oil, containing about 18% of methyl cis-4,4a,5,7a-tetrahydrocyclopenta[b]pyranyl-3-carboxylate. The crude heading compound is subjected to the Wittig reaction, described below, without further purification.

(d) 4-(2-Carbomethoxy-bicyclo[2.2.1]hept-5-enyl-2-(E)-vinylene)-1-tosylindole (IX)

A mixture of 135 mg (5.6 mmol) NaH and 2 ml dry DMSO is heated with stirring under argon at 75° for 45 minutes. 2.8 g (5 mmol) of the phosphonium bromide obtained under (b) in 5 ml DMSO at 10° is rapidly added, the resulting red solution is stirred for 3 minutes, and 1.2 g (5.2 mmol) of the crude aldehyde obtained under (c) are added slowly. The reaction mixture is stirred at room temperature for 16 hours, and evaporated in vacuo. Shaking of the residue with water/ether, evaporation of the dried ($Na_2SO_4$) ether phase and trituration of the residue gives the trans-vinylindole as a solid residue which can be used as described below without further purification; m.p.: 148°-150° after recrystallization from diisopropylether.

(e) 4-(2-Carbomethoxy-bicyclo[2.2.1]hept-5-enyl-2-(E)-vinylene)indole (X)

A solution of 1.6 g (3.58 mmol) of the N-tosylindole obtained under (d) in 32 ml 2N NaOH in methanol is heated at reflux under argon for 1.5 hours. Concentration of the reaction mixture is vacuo, shaking of the residue with water/ether, evaporation of the dried ($Na_2SO_4$) ether phase and flash chromatography (hexane/$CH_2Cl_2$/ethyl acetate (20:2:1) yields the heading compound as an oil.

(f) 3-(2-Nitroethyl)-4-(2-carbomethoxy-bicyclo[2.2.1]hept-5-enyl-2-(E)-vinylene)-indole (XI)

Procedure (a): A mixture of 3 ml acetic acid, 2.5 ml 40% aq. dimethylamine and 1.2 ml 36% aq. formaldehyde is added to a solution of 415 mg (1.42 mmol) of the vinylindole obtained under (e) in 0.4 ml ether. The reaction mixture is stirred at room temperature for 2 hours, then adjusted to pH≧9 with 20% aq. NaOH and extracted with ethyl acetate. Evaporation of the dried ($Na_2SO_4$) extracts and crystallization of the residue yields crystalline 3-(2-N,N-dimethylaminoethyl)-4-(2-carbomethoxy-bicyclo[2.2.1]hept-5-enyl-2-(E)-vinylene)-indole; m.p.: 119°-122°.

After successive addition of 245 mg (4 mmol) nitromethane and 60 mg (0.42 mmol) dimethyl acetylenedicarboxylate to a solution of 135 mg (0.386 mmol) of 3-(2-N,N-dimethyl)-4-(exo-2-carbomethoxy-bicyclo[2.2.1]hept-5-enyl-2-(E)-vinylene)-indole in 3 ml dry tetrahydrofuran under argon, the mixture is stirred at room temperature for 5 hours. Evaporation and chromatography (toluene/ethylacetate 94:6) yields the heading nitroethylindole as an oil.

Procedure (b): 1.6 ml (1.84 mmol) of 1.15M nitroethylene in toluene are added to a solution of 270 mg (0.92 mmol) of the indole obtained under (e) in 5 ml toluene. Stirring of the mixture at room temperature for 66 hours, followed by evaporation and chromatography (toluene/ethylacetate 95:5) yields the heading nitroethylindole.

(g) 3-N-Methoxyiminoethyl-4-(2-carbomethoxy-bicyclo[2.2.1]hept-5-enyl-2-(E)-vinylene)-indole (VI) [Completion of basic step (i)]

158 mg (1.89 mmol) O-Methylhydroxylamine hydrochloride in 9.2 ml (1.89 mmol) 0.205N NaOMe in methanol are added to a solution of 230 mg (0.63 mmol) of the nitroethyl indole obtained under (f) in 3.7 ml (0.76 mmol) 0.205N NaOMe in methanol. A solution of 7.7 g ammonium acetate and 13.9 ml 15% aq. $TiCl_3$ in 24 ml degassed water under argon at 10° is added rapidly to the reaction mixture which is then stirred for 2 hours at 20° and extracted with ether (3x). Washing (aq. $NaHCO_3$, sat. aq. NaCl), drying ($Na_2SO_4$) and evaporation of the ether phase and chromatography of the oily residue in methylene chloride yields a 1:1 mixture of the syn- and anti-isomers of the heading compound.

(h) Methyl 6-methoxy-8-ergolene-8-carboxylate (IV) [Basic steps (ii) and (iii)]

A solution of 73 mg (0.2 mmol) of the compound obtained under (g) in 7.3 ml 1,2,4-trichlorobenzene is added dropwise by means of a syringe drive over 5 hours through a water-cooled reflux condenser into 146 ml 1,2,4-trichlorobenzene, stirred at 200° under argon. Evaporation at 0.1 Torr and chromatography of the residue (methylene chloride/ethyl acetate 39:1) yields the heading compound as an oily 2:3-mixture of diastereoisomers of ergolene I and II respectively.

(i) (±)-Lysergic acid [Basic step (iv)]

8.1 μl (0.672 mmol) methyl fluorosulfonate are added to a solution of 10 mg (0.0336 mmol) of the compound obtained under (h) in 0.5 ml dichloromethane (distilled from $CaH_2$). The mixture is stirred at room temperature for 18 hours and then evaporated to yield a solid residue. This is stirred with 30 ml amalgamated aluminium foil [in tetrahydrofuran/water (2:1) at 0 to +5° for 18 hours]. Evaporation of the filtered reaction mixture and subsequent preparative thin-layer chromatography ($SiO_2$, ethyl acetate/methanol 39:1) yields a mixture of 6-methyl-ergolenes which was heated at reflux in 0.5N KOH in ethanol/$H_2O$ 1:1 (0.7 ml) under nitrogen for 1 hour. Concentration of the solution, followed by acidification with 1N HCl to pH 5.5 leads to the precipitation of crystalline (±)-lysergic acid showing identical $^1$N-NMR and Mass spectra-data as authentic racemic lysergic acid.

The resultant lysergic acid may be resolved into optically active lysergic acid by the method described in A. Stoll et al. Hoppe-Seylers, Z.Physiol. Chem. 250, 7, (1937).

In analogous manner the following compounds may be produced:
12-methoxymethergine
12-hydroxylysergic acid diethylamide
13-bromo-dihydrolysergic acid
using as necessary appropriate hydrogenation reactions to produce any dihydro moiety.

What we claim is:

1. A process for the preparation of an ergot alkaloid of the formula

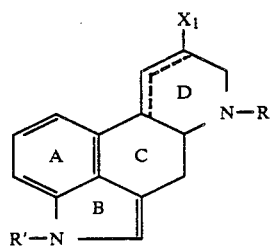

which comprises the step of intramolecularly cyclizing a compound of the formula

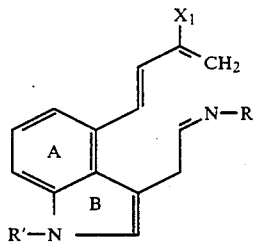

under Diels-Alder reaction conditions, wherein
$X_1$ is a pharmacologically acceptable substituent in the 8-position of an ergot alkaloid or a substituent convertible thereto which is stable under Diels-Alder reaction conditions;
R is $(C_{1-4})$alkoxy, acyloxy, benzyloxy, amino, $(C_{1-4})$alkyl amino, acyl or $(C_{1-4})$alkyl sulphonyl, where acyl is (1-20)alkanoyl, benzoyl or phen$(C_{2-5})$-alkanoyl;
R' is hydrogen, $(C_{1-4})$alkyl, $(C_{1-4})$alkyl carbonyl, $(C_{1-4})$alkoxy carbonyl or tosyl; and
Rings A and B are ergot alkaloid rings, which may be substituted with pharmaceutically acceptable ergot alkaloid ring substituents which are stable under Diels-Alder reaction conditions.

2. A process for the preparation of an ergot alkaloid of the formula

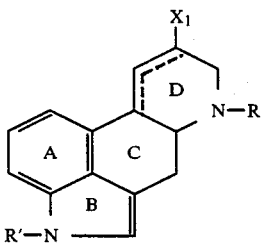

which comprises the step of intramolecularly cyclizing a compound of the formula

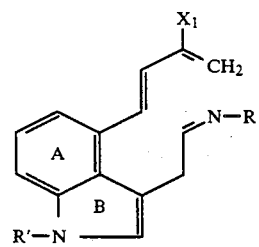

under Diels-Alder reaction conditions, wherein
$X_1$ is cyano, carbamoyl, carbamoyl mono-substituted by $(C_{1-4})$alkyl, carbamoyl disubstituted by $(C_{1-4})$alkyl or $(C_{3-5})$alkylidenyl, —CH$_2$OH or $(C_{1-4})$alkoxy carbonyl;
R is $(C_{1-4})$alkoxy, acyloxy, benzyloxy, amino, $(C_{1-4})$alkyl amino, acyl or $(C_{1-4})$alkyl sulphonyl, where acyl is (1-20)alkanoyl, benzoyl or phen$(C_{2-5})$-alkanoyl;
R' is hydrogen, $(C_{1-4})$alkyl, $(C_{1-4})$alkyl carbonyl, $(C_{1-4})$alkoxy carbonyl or tosyl; and
Rings A and B are ergot alkaloid rings, which may be substituted with pharmaceutically acceptable ergot alkaloid ring substituents which are stable under Diels-Alder reaction conditions.

3. A process according to claim 2 in which $X_1$ is $(C_{1-4})$alkoxy carbonyl.

4. A process according to claim 2 in which $X_1$ is methoxycarbonyl.

5. A process according to claim 2 in which R is $(C_{1-4})$alkoxy.

6. A process according to claim 2 in which the benzyloxy or acyl is substituted with fluorine, chlorine or $(C_{1-4})$alkoxy.

7. A process according to claim 2 in which R' is hydrogen.

8. A process according to claim 2 in which the cyclization is effected at from 180° to 250° C.

9. A process according to claim 2 in which Ring B is substituted in the 2-position.

10. A process for the preparation of an ergot alkaloid of the formula

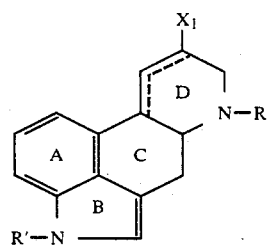

which comprises the step of intramolecularly cyclizing a compound of the formula

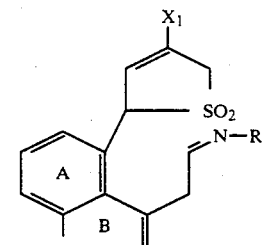

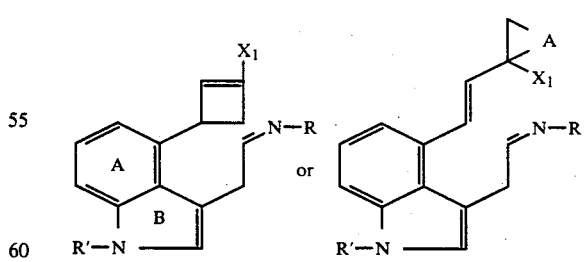

under Diels-Alder reaction conditions, wherein
$X_1$ is cyano, carbamoyl, carbamoyl mono-substituted by $(C_{1-4})$alkyl, carbamoyl disubstituted by $(C_{1-4})$alkyl or $(C_{3-5})$alkylidenyl, —CH$_2$OH or $(C_{1-4})$alkoxy carbonyl;
A is

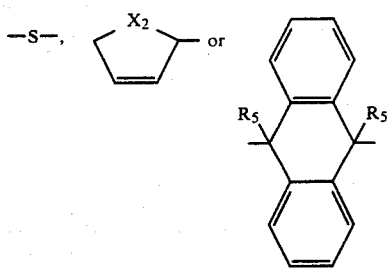

X₂ is oxygen, sulfur, methylene, or methylene substituted with alkylidene of 1 to 4 carbon atoms;

R₅ is hydrogen or (C₁₋₄)alkyl;

R is (C₁₋₄)alkoxy, acyloxy, benzyloxy, amino, (C₁₋₄)alkyl amino, acyl or (C₁₋₄)alkyl sulphonyl, where acyl is (1-20)alkanoyl, benzoyl or phen(C₂₋₅)-alkanoyl;

R' is hydrogen, (C₁₋₄)alkyl, (C₁₋₄)alkyl carbonyl, (C₁₋₄)alkoxy carbonyl or tosyl; and Rings A and B are ergot alkaloid rings, which may be substituted with pharmaceutically acceptable ergot alkaloid ring substituents which are stable under Diels-Alder reaction conditions.

11. A process according to claim 10 in which X₁ is (C₁₋₄)alkoxy carbonyl, R is (C₁₋₄)alkoxy and R' is hydrogen.

12. A process according to claim 10 in which 3-N-methoxyiminoethyl-4-(2-carbomethoxy-bicyclo[2.2.1-]hept-5-enyl-2-(E)-vinylene)-indole is intramolecularly cyclized to form 6-methoxy-8-ergolene-8-carboxylate, methyl ester.

13. A process according to claim 12 in which the 6-methoxy-8-ergolene-8-carboxylate, methyl ester is deprotected to yield lysergic acid.

14. A process according to claim 10 in which the ergot alkaloid is converted into a pharmaceutically active ergot alkaloid derivative.

15. A process according to claim 14 in which the ergot alkaloid derivative is 12-hydroxylysergic acid diethylamide, 13-bromo-dihydrolysergic acid, 2,13-dibromo-dihydrolysergic acid glycinamide, 2-chloro-6-methyl-8β-cyanomethylergoline, 1-methyl-dihydrolysergol, 1-formyl-dihydro-homolysergic acid nitrile, 12-hydroxy-dihydroergometrine 2-methyl-α-ergocryptine, 2-methyl-lysergic acid or 12-methoxymethergine.

16. A process according to claim 10 in which X₁ is (C₁₋₄)alkoxy carbonyl.

17. A process according to claim 10 in which X₁ is methoxycarbonyl.

18. A process according to claim 10 in which R is (C₁₋₄)alkoxy.

19. A process according to claim 10 in which R' is hydrogen.

20. A process according to claim 10 in which the cyclization is effected at from 180° to 250° C.

21. A process according to claim 10 in which Ring B is substituted in the 2-position.

* * * * *